United States Patent
Woodward

(10) Patent No.: US 10,421,981 B2
(45) Date of Patent: Sep. 24, 2019

(54) METHODS AND SYSTEMS FOR PRODUCING SHORT CHAIN WEAK ORGANIC ACIDS FROM CARBON DIOXIDE

(71) Applicant: Big Monkey Services, LLC, Evanston, WY (US)

(72) Inventor: Brian C. Woodward, Evanston, WY (US)

(73) Assignee: Big Monkey Services, LLC, Evanston, WY (US)

( * ) Notice: Subject to any disclaimer, the term of this patent is extended or adjusted under 35 U.S.C. 154(b) by 0 days.

(21) Appl. No.: 15/437,662

(22) Filed: Feb. 21, 2017

(65) Prior Publication Data

US 2018/0237808 A1 Aug. 23, 2018

(51) Int. Cl.
*C12P 7/40* (2006.01)
*C12P 7/56* (2006.01)
(Continued)

(52) U.S. Cl.
CPC .......... *C12P 7/40* (2013.01); *C12P 7/52* (2013.01); *C12P 7/54* (2013.01); *C12P 7/56* (2013.01)

(58) Field of Classification Search
CPC ...... C02F 3/341; C02F 3/348; C02F 2101/22; C02F 2103/18; C02F 2101/106; C02F 2101/103; C02F 2101/20; B01D 53/502; B01D 53/64; B01D 53/84; B01D 2257/60; B01D 2257/302; B01D 2257/206; B01D 2257/2045; B01D 2258/0291; B01D 2251/606; B01D 2251/604; B01D 2251/404; B01D 2251/402;
(Continued)

(56) References Cited

U.S. PATENT DOCUMENTS 4,834,955 A    5/1989 Mouche
6,056,934 A    5/2000 Carlsen et al.
(Continued)

OTHER PUBLICATIONS

Carrieri Damian et al. "Enhancing photo-catalytic production of organic acids in the cyanobacterium *Synechocytis* sp. PPC 6803 DglgC, a strain incapable of glycogen storage". Microbial Biotechnology Mar. 2015; 8(2): 275-280 (Year: 2015).*
(Continued)

*Primary Examiner* — Michael L Hobbs
(74) *Attorney, Agent, or Firm* — Workman Nydegger

(57) ABSTRACT

Methods and systems for producing short carbon chain weak organic acids (e.g., acetic acid) from a gas stream rich in carbon dioxide. The systems include a liquid-gas contact unit a flue gas desulfurization unit), and a bacterial strain disposed in the liquid-gas contact unit. The bacterial strain reduces a concentration of carbon dioxide in the gas stream, and produces one or more organic acids (e.g., acetic acid, butyric acid, propionic acid, lactic acid, or combinations thereof). Related methods include providing a gas stream rich in carbon dioxide, introducing the gas stream into a liquid-gas contact unit, preparing an inoculum comprising a bacterial strain adapted to produce organic acid(s) from the carbon in the gas stream, and inoculating the liquid-gas contact unit with first amount of the inoculum such that the bacteria therein consume carbon dioxide from the gas stream, producing the organic acid(s).

14 Claims, 3 Drawing Sheets

(51) Int. Cl.
*C12P 7/54* (2006.01)
*C12P 7/52* (2006.01)

(58) Field of Classification Search
CPC .. B01D 2251/304; B01D 53/83; B01D 53/75; B01D 2258/0283; B01D 2253/102; B01D 2251/95
See application file for complete search history.

(56) References Cited

U.S. PATENT DOCUMENTS

| | | | |
|---|---|---|---|
| 6,656,249 | B1 | 12/2003 | Buisman et al. |
| 7,060,233 | B1 | 6/2006 | Srinivas et al. |
| 7,325,603 | B2 | 2/2008 | Kotlar |
| 7,531,159 | B2 | 5/2009 | Lanning et al. |
| 8,070,863 | B2 | 12/2011 | Tsangaris et al. |
| 8,306,665 | B2 | 11/2012 | Tsangaris et al. |
| 8,353,980 | B2 | 1/2013 | Murphy |
| 8,372,169 | B2 | 2/2013 | Tsangaris et al. |
| 8,413,967 | B2 | 4/2013 | Johnson et al. |
| 8,690,975 | B2 | 4/2014 | Tsangaris et al. |
| 10,046,274 | B2 * | 8/2018 | Woodward ............... F23J 15/04 |
| 2007/0092962 | A1 * | 4/2007 | Sheppard ............... C12M 21/02 435/266 |
| 2012/0115201 | A1 | 5/2012 | Adams |
| 2015/0125901 | A1 * | 5/2015 | Razavi-Shirazi ....... C02F 3/108 435/42 |

OTHER PUBLICATIONS

U.S. Appl. No. 14/839,037, filed Aug. 28, 2015, Woodward.
U.S. Appl. No. 15/165,751, filed May 26, 2017, Woodward.
Nolan, Paul S., "Flue Gas Desulfurization Technologies for Coal-Fired Power Plants," Presented at the Coal-Tech 2000 International Conference, Nov. 13-14, 2000, Jakarta Indonesia, 13 pages.
Mortson, Murray, et al., "Flue Gas Desulfurization Using Recycled Sodium Bicarbonate," Presented at the US EPA/DOE/EPRI Combined Power Plant Air Pollutant Control Symposium: "The Mega Symposium," on Aug. 20-23, 2001, Chicago, IL, US, 6 pages.
"Flue-Gas Desulfurization," Wikipedia, the free encyclopedia, Accessed Aug. 15, 2016 at https://en.wikipedia.org/wiki/Flue-gas_desulfurization 8 pages.
"Naughton Plant," PacfiCorp, Jan. 2011, 2 pages.
Srivastava, R.K., et al., "Flue Gas Desulfuization: The State of the Art," Journal of Air and Waste Management Association, Dec. 2001 vol. 51, pp. 1676-1688.
U.S. Appl. No. 15/165,751, filed Aug. 31, 2018, Office Action.
U.S. Appl. No. 15/165,751, filed Jan. 10, 2019, Notice of Allowance.
Sun, et al. Abstract of "Study on Sale Inhibition Properties of Gama-PGA," Journal of East China Normal University, May 2010, 3 pages.
Office Action for U.S. Appl. No. 14/839,037 dated Nov. 17, 2017, 17 pages.

* cited by examiner

METHODS AND SYSTEMS FOR PRODUCING SHORT CHAIN WEAK ORGANIC ACIDS FROM CARBON DIOXIDE

BACKGROUND

Coal-fired electricity-generating plants account for a substantial portion of the approximately 1.05 billion tons of coal burned each year in the United States. Such power plants emit 1.9 billion tons of carbon dioxide each year. Relatively recently, there has been an increased interest in how to reduce such carbon dioxide emissions, as carbon dioxide is known to act as a "greenhouse gas", such that increasing concentrations of carbon dioxide in the atmosphere may play a role in increasing temperatures and/or climate change.

While various proposals exist for collecting, sequestering, and storing carbon dioxide, serious difficulties exist with commercializing any such proposals, often because due to cost constraints and other issues, their implementation is not practical. As such, there continues to exist a need for simple, inexpensive, and effective means for reducing carbon dioxide emissions.

SUMMARY

Described herein are various methods and systems for manufacture of short carbon chain (e.g., 1-5, or 2-4 carbons) weak organic acids from a gas stream rich in carbon dioxide. Such systems and methods could also be used for terraforming an atmosphere (e.g., fighting to reduce or slow an increase in $CO_2$ concentrations in an atmosphere). By way of example, one such system may include a liquid-gas contact unit, and a bacterial strain disposed in the liquid-gas contact unit, where the bacterial strain reduces a concentration of carbon dioxide in the gas stream (e.g., by at least 10%), and produces one or more organic acids therefrom. Such organic acids may include, but are not necessarily limited to, acetic acid, butyric acid, propionic acid, lactic acid, and combinations thereof. Importantly, the methods and systems are not typically intended to produce methane or other biogas, but to consume carbon dioxide in the gas stream in order to produce weak organic acids, as noted above. For example, while various attempts have been described where carbon dioxide may be used to produce methane or another biogas (e.g., see U.S. 2012/0115201 to Adams), such methods and systems include their own problems associated with the production of such biogas, as such methane or other biogas products must then be carefully handled, accounted for, and disposed of (or used) in accordance with numerous EPA or other regulatory requirements. This is particularly so, given that methane is far more potent as a greenhouse gas than is carbon dioxide. Thus, efforts to curb carbon dioxide emission through generation of methane or other biogas in at least some respects, replaces one problem with another that may be far more cumbersome. Thus, in at least some embodiments of the present systems and methods, no appreciable amount of methane or other biogas is produced. In some embodiments, the only significant product produced by the methods and systems may be organic acids such as those described herein.

In some embodiments, the gas stream may be a flue gas, e.g., such as the flue gas of a coal-fired or other power plant, or other industrial gas stream that is rich in carbon dioxide. In some embodiments, the liquid-gas contact unit may be a flue gas treatment unit (e.g., a flue gas desulfurization unit).

Another embodiment is directed to a method for producing short chain weak organic acids, the method including providing a gas stream that is rich in carbon dioxide, introducing the gas stream into a liquid-gas contact unit, and preparing an inoculum that includes a bacterial strain adapted produce one or more organic acids from carbon dioxide in the gas stream. The liquid-gas contact unit is inoculated with a first amount of the inoculum, such that the bacteria of the bacterial strain are present within the liquid-gas contact unit to consume carbon dioxide from the gas stream and to produce one or more organic acids therefrom. As noted above, preferably, the bacteria do not produce any appreciable volume of methane or other biogas. Furthermore, the bacteria may be adapted to reduce the concentration of carbon dioxide in the gas stream by more than 10%, (e.g., at least 15%, at least 20%, at least 25%, at least 30%, at least 35%, at least 40%, at least 45%, or at least 50%, or even more).

In an embodiment, the bacterial strains responsible for promoting production of the organic acids may be reclaimed (e.g., periodically or continuously), and reintroduced (e.g., recycled) into the liquid-gas contact unit. Additional bacterial strains adapted to perform different functions than organic acid production may also be introduced into the liquid-gas contact unit (i.e., two differently adapted bacterial strains, serving different purposes, may be present). For example, a separate bacterial strain may be introduced into a flue-gas desulfurization unit with the organic acid promoting bacterial strain, to inhibit crystalline buildup therein. Another contemplated bacterial strain may be particularly adapted to remediate heavy metals.

The liquid in a liquid-gas contact unit naturally contains water and may include other nutrients and otherwise be amenable to the growth and proliferation of the selected bacterial strain(s). In some embodiments, the above described methods may further include allowing the bacteria to proliferate in the at least one liquid-gas contact unit for a selected period of time, and/or until a selected cell density is achieved, after which the bacteria and/or other materials therein may be recovered from the liquid-gas contact unit. The bacteria that are recovered may be recycled for reuse. For example, such methods may include re-inoculating the liquid-gas contact unit with a fresh bacterial inoculum, with recycled bacteria inoculum, a mixture thereof, or the like.

In a preferred embodiment of the presently described systems and methods the bacterial inoculum that promotes organic acid production comprises at least one of *Pediococcus, Propionibacterium*, such as *Pediococcus* sp., *Propionibacterium* sp., combinations thereof, and/or variants thereof. More specifically, preferred species may include at least one of *Pediococcus acidilacti, Propionibacterium freudenreichii*, and combinations and/or variants thereof.

These and other objects and features of the present invention will become more fully apparent from the following description and appended claims, or may be learned by the practice of the invention as set forth hereinafter.

DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Definitions

Figure 1:
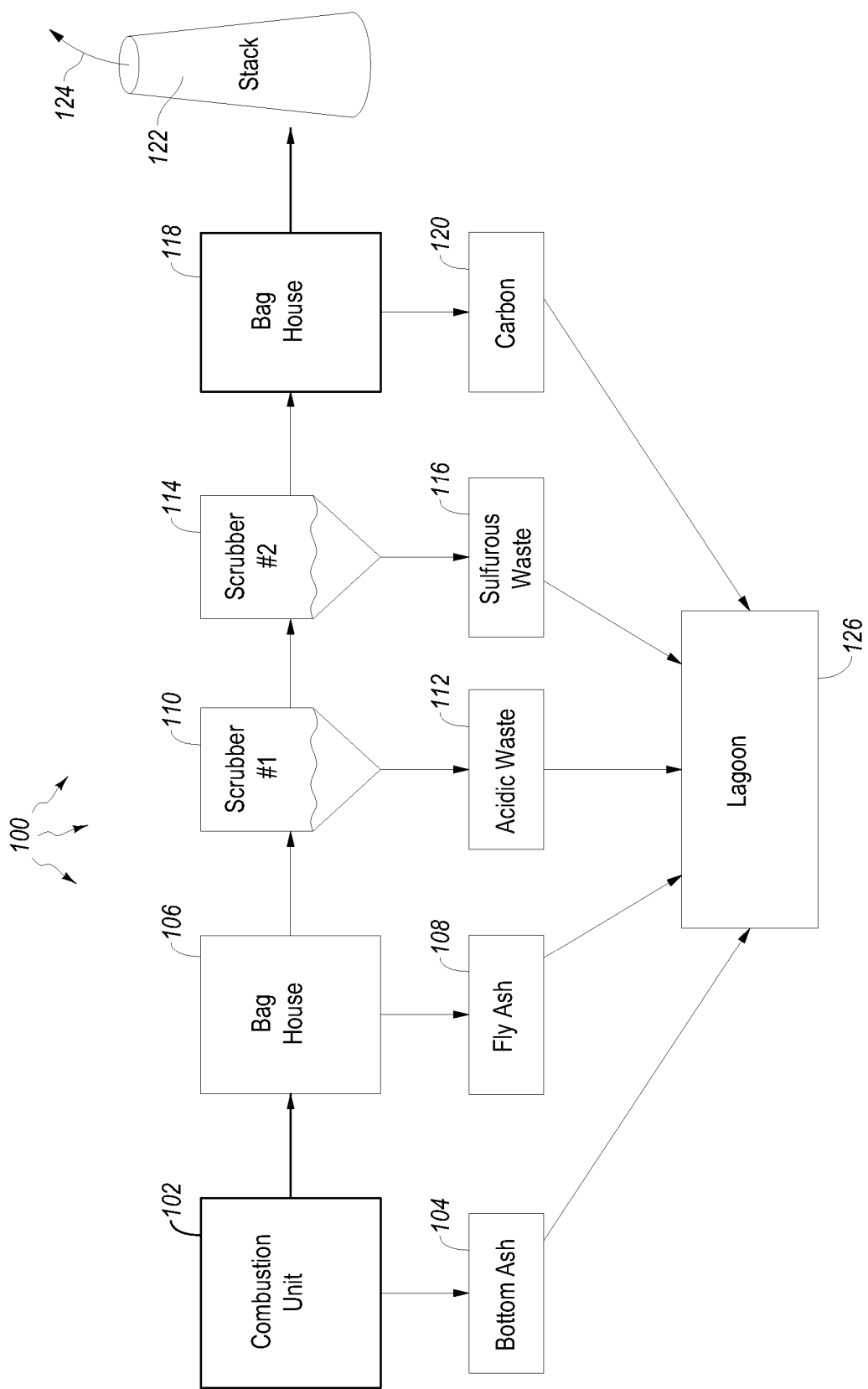
FIG. 1 is a schematic illustration of an exemplary power plant with a flue gas treatment system that includes dry and liquid waste recovery systems.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes one, two or more surfactants.

Numbers, percentages, ratios, or other values stated herein may include that value, and also other values that are about or approximately the stated value, as would be appreciated by one of ordinary skill in the art. A stated value should therefore be interpreted broadly enough to encompass values that are at least close enough to the stated value to perform a desired function or achieve a desired result, and/or values that round to the stated value. The stated values include at least the variation to be expected in a typical manufacturing or formulation process, and may include values that are within 10%, within 5%, within 1%, etc. of a stated value. Furthermore, the terms "substantially", "similarly", "about" or "approximately" as used herein represent an amount or state close to the stated amount or state that still performs a desired function or achieves a desired result. For example, the term "substantially" "about" or "approximately" may refer to an amount that is within 10% of, within 5% of, or within 1% of, a stated amount or value.

Some ranges may be disclosed herein. Additional ranges may be defined between any values disclosed herein as being exemplary of a particular parameter. All such ranges are contemplated and within the scope of the present disclosure.

II. Introduction

Described herein are methods and systems for producing short chain weak organic acids from a gas stream that is rich in carbon dioxide. Such a gas stream may be a flue gas stream from a power plant (e.g., fired by coal, natural gas, petroleum, solid waste, biomass, etc.), or other combustion plant that may generate a significant volume of carbon dioxide. Rather than venting the carbon dioxide to the atmosphere, or attempting to sequester and store the carbon dioxide through some complex (and typically expensive and often impractical) mechanism, the present systems and methods use the gaseous carbon (e.g., principally carbon dioxide) in the gas stream to produce one or more organic acids, e.g., typically organic acids having a relatively short carbon chain length (e.g., 1 to 5 carbon atoms, 2 to 4 carbon atoms, or 2 to 3 carbon atoms).

The systems described in the present application include at least one liquid-gas contact unit (e.g., which may be a flue gas scrubber unit such as a flue gas desulfurization unit) that includes one or more selected bacterial strains disposed therein that are specifically adapted to consume at least a portion of the carbon dioxide in the gas stream and convert it into one or more organic acids. Exemplary organic acids formed according to the present systems and methods include acetic acid, butyric acid, propionic acid, and/or lactic acid. Production of such organic acids may be relatively selective, such that the production of any unwanted bioproducts, such as methane or other biogas, is negligible. For example, in addition to reducing selectively and production of the desired organic acids, production of methane or other biogas products attributable to action of the bacteria would present a problem in that it results in the presence of new hazardous materials, which materials themselves typically require special handling, collection, and disposal. For example, the EPA and/or other regulatory agencies lay stringent requirements on any such methane or biogas that may be produced. Thus, according to at least some embodiments of the present disclosure, the target products produced within the present systems and methods are carefully controlled to ensure high selectivity in the products produced by the bacterial strain(s) in the liquid-gas contact unit. For example, in at least some embodiments, no methane or other biogas is produced. The only significant products produced in the liquid-gas contact unit by the bacterial strains may be the targeted organic acids, as well as harmless byproducts of respiration or other biological processes such as water, some carbon dioxide (although the process exhibits a net decrease in $CO_2$ concentration), biomass (new cell growth), and the like. Methods include inoculating the liquid-gas contact unit with one or more selected bacteria that consume carbon dioxide and produce one or more organic acids therefrom. Methods may include periodic re-inoculation of the liquid-gas contact unit with fresh bacteria and/or periodic recovery of the bacteria from the liquid-gas contact unit.

III. Systems and Methods for Organic Acid Production

Referring to FIG. 1, a power plant 100 that generates a gas stream rich in carbon dioxide is shown. FIG. 1 shows a general overall treatment regime, with treatment of various streams that may include one or more of dry, liquid, and/or gaseous waste streams, which may undergo various treatments. In the illustrated embodiment, burning of the combustible material (e.g., coal, natural gas, petroleum, biomass, solid waste, or the like) produces a variety of waste materials. While FIG. 1 may be described principally in the context of a power plant, those of skill in the art will appreciate that any industrial combustion system that generates a gas stream rich in carbon dioxide may benefit from the technologies described herein.

The power plant 100 illustrated in FIG. 1 includes a combustion unit 102 (e.g., a boiler) that is configured for burning combustible materials (e.g., coal, diesel, fuel oil, other petroleum product, natural gas, municipal solid waste, etc.). Burning of the combustible materials can, for example, be linked to the production of steam to drive a turbine for electrical generation or other energy recovery from the combustible materials. Downstream of the combustion unit 102, the plant may include one or more waste treatment units that are designed to "clean" the combustion gases destined for the stack 122.

In the system illustrated in FIG. 1, downstream from the combustion unit 102 there is illustrated a first bag house 106. A baghouse is an air pollution control device that removes particulates out of air or gas released from commercial processes or combustion for electricity generation by passing the flue gas through long fabric filter tubes (or bags). The first stage of pollution control at a power plant like plant 100 may include an electrostatic precipitator instead of or in addition to a bag house. However, unlike electrostatic precipitators, where performance may vary significantly depending on process and electrical conditions, properly functioning baghouses typically have a particulate collection efficiency of 99% or better, even when particle size is very small.

Downstream from the first baghouse 106, are first and second liquid-gas contact scrubbers 110 and 114 that remove additional pollutants from the flue gas. In the illustrated embodiment, the first scrubber 110 is an acid gas scrubber a hydrochloric acid scrubber) that is configured to remove acidic gases from the flue gas and the second scrubber 114 is a flue-gas desulfurization unit (FGD unit) that is designed to remove sulfur dioxide and other sulfurous gases from the flue gas, although other configurations are of course possible.

As will be explained in greater detail below, the first and second liquid-gas contact scrubbers 110 and 114 clean the flue gas by contacting the gas in the scrubber unit with a liquid medium that is specifically designed to chemically trap certain pollutants (e.g., acidic and/or sulfur containing combustion gases such as HCl, $H_2S$, $SO_2$, and the like). Many heavy metals entrained in the flue gas may also become dissolved or suspended in the liquid contact media.

Downstream from the first and second liquid-gas contact scrubbers 110 and 114 is illustrated a second baghouse 118. The second bag house 118 may include a sorbent injection system that allows the baghouse 118 to extract any remaining heavy metals or dioxins out of the flue-gas with the aid of active carbon (120) before the flue gas is released to the atmosphere 124 through stack 122.

One will appreciate that the foregoing is merely descriptive of some of the components of a power plant and is likely very simplified. Plant 100 may include more or fewer or different components without departing from the spirit of the present invention.

Baghouses 106 and 118 may typically remove heavy metals and other particulates from the flue gas. Scrubbers 110 and 114 may be particularly configured to remove acidic waste and sulfurous waste, respectively, from the flue gas. Bottom ash 104, fly ash 108, acidic waste 112, sulfurous waste 116 and activated carbon 120 used in recovery of mercury or other heavy metals may result therefrom, which waste streams may be further remediated in lagoon 126, using, e.g., technologies described in the inventor's earlier U.S. patent application Ser. No. 15/165,751, filed May 26, 2016, herein incorporated by reference in its entirety. U.S. patent application Ser. No. 15/165,751 describes systems and methods for specifically remediating heavy metals typically present within such waste streams, using one or more particularly selected bacterial strains that are adapted to retain, isolate, and/or otherwise remediate target heavy metals.

The present invention, in at least one aspect, is directed to methods and systems for using the gas stream from combustion unit 102, which gas stream is rich in carbon dioxide, to produce one or more organic acids using one or more bacterial strains particularly adapted to this purpose. Such production may occur in a liquid-gas contact unit. In sonic embodiments, the liquid-gas contact unit may be a scrubber, such as a flue gas desulfurization unit (e.g., scrubber 114) and/or acidic gas scrubber 110, as will be explained in further detail below.

In one embodiment of the present disclosure, bacteria introduced into one or more liquid-gas contact units incorporated into plant 100 may be allowed to proliferate in the liquid-gas contact unit for a selected period of time (e.g., hours, days, weeks, or months). In the case of the scrubber units described above, bacteria may be allowed to proliferate in the scrubber solution (e.g., in scrubber 114) until the solution is spent and the solution is flushed so that it can be replaced with fresh solution, which may occur periodically (e.g., once every 1-6 months, every 2-6 months, or every 4-6 months). In at least sonic embodiments, viable bacteria in the spent solution that is flushed may be reclaimed, and re-introduced into the same or another liquid-gas contact unit (i.e., the unit may be re-inoculated, e.g., using recycled bacteria). In addition or alternative to flushing or other removal of the bacteria that may occur periodically in the liquid-gas contact unit, an additional dose of the selected bacterial strain may be introduced into the scrubber or other liquid-gas contact unit at periodic intervals, e.g., between flushings of scrubber solution.

In one embodiment, bacteria may be allowed to proliferate until they reach a predetermined cell density. In an embodiment, the growth of the bacteria in one or more liquid-gas contact units may be monitored, e.g., by testing for viable cells, by monitoring cell density, by monitoring concentration of organic acids in the liquid solution, by monitoring carbon dioxide levels in the gas stream exiting (as compared to concentration entering) the inoculated liquid-gas contact unit, or the like. Such data may aid the operator in determining if the bacteria are still able to remove $CO_2$ from the gas stream and produce organic acid(s) therefrom, giving the operator some indication of the health of the bacterial culture. For example, cell proliferation may be allowed to proceed as long as the culture in the at least one liquid-gas contact unit is healthy and, presumably, still able to produce organic acid(s) from the carbon dioxide in the gas stream.

Periodically, bacteria may be recovered from the one or more liquid-gas contact units. Such recovered bacteria may be re-introduced into a liquid-gas contact unit, if desired (e.g., optionally after being further cultured and/or nurtured outside of the liquid-gas contact unit with desired nutrients, undergoing cleaning, or other procedures). It may be desirable to periodically recover the bacteria from the at least one liquid-gas contact unit so that the unit can be inoculated with a fresh bacterial culture and/or to prevent dead cells from settling, decaying, and the like. Bacteria may be recovered from a scrubber solution or other solution used in the liquid-gas contact unit by, for example, filtration, flocculation of the bacteria, or other appropriate method. Flocculation, which may be accomplished, for example, by adding magnesium or other appropriate salts to the liquid in the liquid-gas contact unit, is an economical and efficient way to recover the bacteria from the at least one liquid-gas contact unit.

Where bacteria are periodically recovered from the solution present in the liquid-gas contact unit, the liquid-gas contact unit may he reinoculated with a fresh bacterial inoculum. As described above, even where periodic removal and replacement may occur, there may be a more frequent re-inoculation of the liquid-gas contact unit with fresh inoculum. For example, a first amount of the bacterial inoculum may be introduced into the liquid-gas contact unit at a given time. Thereafter, second amounts of bacterial inoculum may also be introduced into the liquid-gas contact unit. The second amounts (e.g., a sort of "booster") may typically be smaller than the first amount.

A number of bacterial, proteobacterial, and archaeal species can be used in the systems and methods described herein. For purposes of simplicity, the term "bacterial strain"

or "bacteria" may be used to refer to all such organisms (e.g., bacterial, proteobacterial, and archaeal species), including both bacterial and archaeal taxonomic domains. Examples of bacterial strains that may be employed herein to produce organic acids using a gas stream rich in carbon dioxide include the genuses *Pediococcus, Propionibacterium*, variants thereof, combinations thereof, and the like. In one embodiment, the bacteria used in the systems and methods described herein includes a biosurfactant and/or biofilm producing bacterium.

In an embodiment, the bacteria may be *Pediococcus* sp., *Propionibacterium* sp., combinations thereof, or variants thereof. In a preferred embodiment, the bacteria used in the systems and methods described herein are *Pediococcus acidilacti, Propionibacterium freudenreichii*, and variants thereof.

While such bacteria are selected for their ability to produce organic acids from carbon dioxide in the gas stream (thereby significantly reducing the concentration of carbon dioxide in the flue gas or other gas stream), in some embodiments, additional bacterial strains adapted to perform a different function may also be introduced into the liquid-gas contact unit. For example, in some embodiments, another bacterial strain may be introduced which is adapted to inhibit crystal formation (e.g., on contact plates in the scrubber unit), which otherwise can result in periodic plugging of contact surfaces within the liquid-gas contact unit. By way of further example, in some embodiments another bacterial strain adapted to remediate heavy metals may be introduced into the liquid-gas contact unit (or another treatment unit, such as lagoon 126).

As will be explained in further detail below, the liquid-gas contact unit may include a contact plate or screen including holes formed therein. During operation of a flue-gas desulfurization or other liquid-gas contact unit, such small holes may become at least partially plugged, increasing pressure drop through the unit, requiring additional power (e.g., at a blower or the like) to force the gas stream through the screens, contact plates or similar. Such plugging due to crystal growth may occur as various minerals present in the liquid solution and/or the gas stream precipitate out of solution, forming such crystals, e.g., around the holes of the contact plates or screens, progressively plugging the holes. Examples of bacterial strains that may be introduced into the liquid-gas contact unit in order to inhibit such crystal growth or formation may include bacteria from the genus *Bacillus*, such as *Bacillus subtilis, Bacillus chitinosporus*, variants thereof, combinations thereof, and the like. Additional details of suitable bacterial strains for inhibiting crystal growth are disclosed in Applicant's earlier filed U.S. patent application Ser. No. 14/839,037, filed Aug. 28, 2015, incorporated herein by reference in its entirety.

The liquid-gas contact unit may additionally or alternatively include a bacterial strain adapted to remediate heavy metals. Examples of such bacterial strains may also come from the genus *Bacillus*, examples of which include *Bacillus amyloliquefaciens, Bacillus licheniformis*, variants thereof, combinations thereof, and the like. Additional details of suitable bacterial strains for remediating heavy metals are disclosed in Applicant's earlier filed U.S. patent application Ser. No. 15/165,751, filed May 26, 2016, also incorporated herein by reference in its entirety.

The bacterial strains used in the systems and methods described herein may be grown in any conventional growth medium that supports bacterial growth. Examples of suitable broth for culturing *Pediococcus* sp., *Propionibacterium* sp. and/or *Bacillus* sp. include but are not limited to, a broth composed of peptone, dextrose, yeast extract and malt extract and a broth using the same ingredients as well as proflo cottonseed extract and soy flour. Solid substrates are also suitable for growing such strains. Growth procedures may also be readily scaled up to large fermenters by methods well known in the art.

In one embodiment, the bacterial strain(s) used to produce organic acid(s) from carbon dioxide in the gas stream in the systems described herein may be delivered to the site of use in dry form. Bacteria may be grown and subsequently lyophilized (e.g., freeze-dried) by methods well known in the art. Likewise, the bacterial strain(s) used to produce organic acid(s) in the systems described herein may be delivered to the site of use in liquid media. Bacteria may be grown and subsequently stored in liquid media by methods well known in the art. Bacteria adapted for other purposes (e.g., crystal inhibition and/or heavy metal remediation) may similarly be provided in dry form, and/or in liquid media.

All microbes require nutrient components, C:N:P:S:vitamins: and others, in specific ratios to grow and metabolize target materials. Any imbalance in these ratios can slow or halt microbial growth. Microbes tolerant to higher salt and ionic strength may be naturally adapted to grow in solutions used to treat a high volume of flue gases, and which therefore may include relatively high salt and/or ionic concentrations.

Considerable enhancement of microbial growth and metabolism can be obtained by providing and maintaining the proper microbial population, proper environment, and proper nutrient component balance. For example, with the addition (e.g., staged and/or cyclical addition) of appropriate microbes, nutrients, and environmental adjustment components at various points, significant production of organic acid(s) and reduction of carbon dioxide concentration in flue gas released from stack 122 is possible.

Figure 2A:
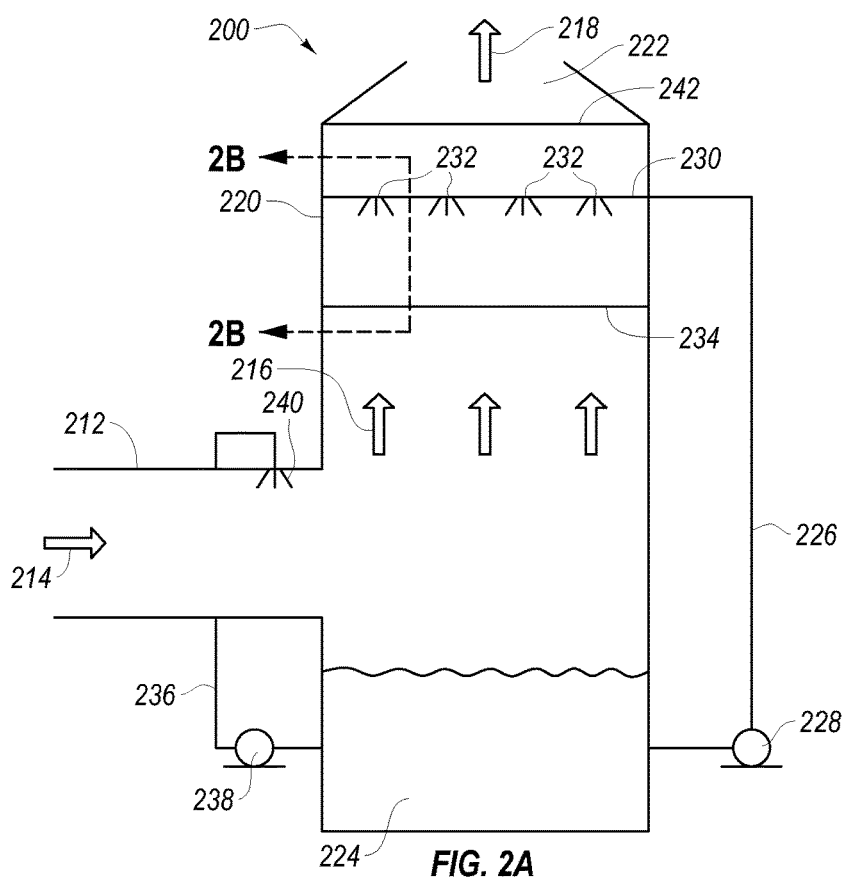
FIGS. 2A-2B illustrate a cutaway view of a liquid-gas contact unit (e.g., a flue gas desulfurization unit), according to one embodiment of the present disclosure.
Figure 2B:
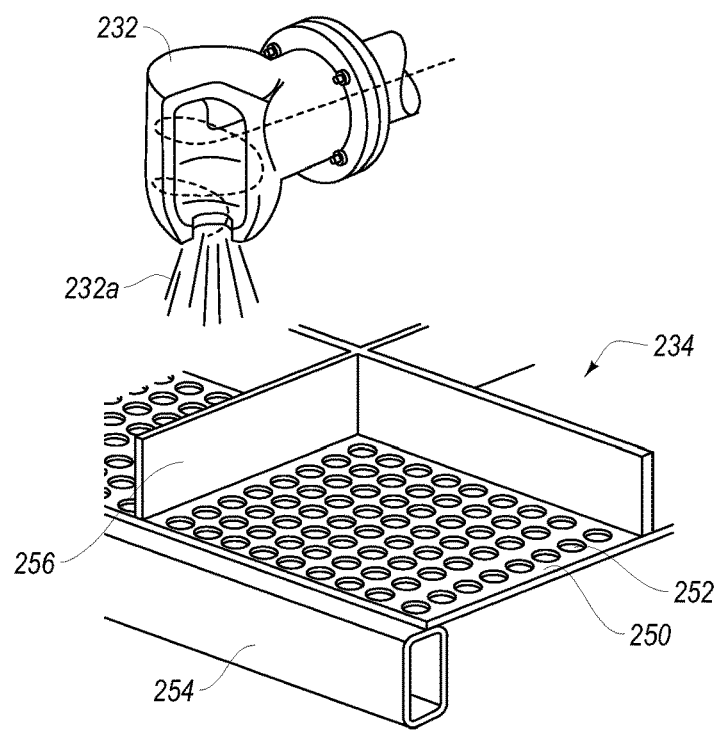

Referring now to FIGS. 2A and 2B, an exemplary liquid-gas contact unit 200 is schematically illustrated. Such a liquid-gas contact unit may be a flue gas desulfurization "FGD" unit (e.g., scrubber 114), an acid gas scrubber a hydrochloric acid scrubber, such as scrubber 110), or another type of liquid-gas contact unit.

The liquid-gas contact unit 200 includes a vessel 220 that serves to house the liquid-gas contact scrubber unit 200. Gas stream 214 (e.g., flue gas, rich in carbon dioxide) enters the vessel 220 through inlet duct 212. The gas stream drifts or is forced up through the vessel 220 as depicted at 216; the cleaned flue gas 218 exits the vessel 220 at outlet 222. Prior to exiting the liquid-gas contact unit 200, the flue gas or other gas stream, which typically carries significant water vapor due to the nature of the liquid-gas contact process, may be dewatered by passing through a condensation unit 242. The cleaned flue gas 218 may be discharged directly to the air (e.g., through a stack 122) or be sent for further processing (e.g., another scrubber unit, a bag house, or the like).

As illustrated in FIG. 2A, the vessel 220 may include a reservoir of liquid 224 (e.g., a desulfurization agent). The unit 200 typically uses a water-based solution to capture pollutants in the flue gas or other gas stream by absorbing the pollutants from the carrier gas stream 214, 216. The scrubbing liquid 224 typically contains a reactive agent that "neutralizes" the absorbed pollutant (e.g., $SO_2$, $H_2S$, HCl, or the like). In the case of an acid scrubber, the absorption liquid may contain a base (e.g., NaOH) that can neutralize the captured acid. A FGD unit may contain a desulfurization agent that may include calcium carbonate (limestone), calcium-magnesium carbonate (dolomite), calcium oxide, calcium hydroxide Ca(OH)$_2$, sodium carbonate (Na$_2$CO$_3$), sodium. hydroxide (NaOH), magnesium hydroxide (Mg(OH)$_2$), combinations thereof, or the like. In an alternative embodiment, the reservoir of absorption liquid 224 may be external to the vessel 220 of unit 200. In an embodiment, the absorption liquid 224 may be inoculated with one or more types of bacteria that are adapted to grow in the absorption liquid and to produce one or more organic acids from the gas stream 214.

In any case, the reservoir of liquid 224 may be connected to a spray bar 230 and a plurality of sprayers 232 via a first recirculation line 226 and a first recirculation pump 228. FIG. 1B illustrates an exemplary sprayer 232. As the flue gas or other gas stream 216 rises through the vessel 220, the first recirculation line 226 and a first recirculation pump 228 draw liquid from the reservoir 224 and deliver it to the sprayers 232. Target components in the relatively hot, rising flue gas 216 react with the chemicals in the liquid (e.g., calcium carbonate) sprayed down to extract target pollutants (e.g., HCl, H$_2$S, and/or SO$_2$) from the gas stream 216. In many liquid-gas contact scrubber units, the absorption liquid 224 is sprayed onto a contact plate 234 that is configured to increase the surface area of contact between the flue gas and the absorption liquid. An exemplary contact plate 234 is shown in FIG. 2B, which will be discussed in greater detail below.

In the illustrated embodiment, the system 200 is illustrated as further including a presaturation sprayer 240 that pre-contacts the hot flue gas 214 with the absorption liquid 224 prior to the gas entering the vessel 220 (e.g., in inlet duct 212). The pre-saturation sprayer 240 may be fluidly connected to the reservoir of absorption liquid 224 via a second recirculation line 236 and a recirculation pump 238.

Referring now to FIG. 2B, an exemplary spray head 232 and contact plate 234 that can be used in liquid-gas contact unit 200 to increase the surface area for gas-liquid contact are illustrated in greater detail. The spray head 232 can have a number of possible sizes and configurations depending on the size and capacity of the liquid-gas contact unit 200. For instance, at a typical power generation station, a liquid-gas contact unit (e.g., a flue gas desulfurization unit) may have a vessel 220 as large as 20-40 feet in diameter and each spray head may be 6 to 18 inches in diameter. The pre-saturation sprayers 240 may be similar to the sprayers 232. In a typical liquid-gas contact unit 200, the contact plates 234 may include a number of screens or perforated plates 250 that may each include hundreds (or more) of small holes 252 drilled, punched, or otherwise formed therein. In the illustrated embodiment, the screens or perforated plates 250 are supported between upper supports 256 and lower supports 254.

In the illustrated operation, the spray head 232 sprays the contact liquid 224 inoculated with selected bacterial strain(s) down onto the contact plate 234. As the flue gas 216 flows up through the vessel 220, the flue gas 216 passes through holes 252 that are coated with the contact liquid 224.

Liquid-gas contact scrubber units can be configured not only to efficiently remove acidic waste (e.g., HCl) and/or sulfurous waste (e.g., $SO_2$, $H_2S$) through action of reactive agent(s) that "neutralize" the target pollutant present in the gas stream, but also to remove a significant fraction of the carbon dioxide and/or carbon monoxide present within the gas stream, through action of the one or more bacterial strain(s) specifically inoculated into the unit 200 as a whole, particularly the contact liquid 224. Such $CO_2$ removal and organic acid production does not require any significant increased residence time in liquid-gas contact unit 200, as compared to that employed for removing typical target materials (e.g., $SO_2$). Rather, the reductions and organic acid production described herein occurs while maintaining substantially the same residence times as employed for typical scrubbing operations, offering simultaneous removal of $CO_2$ (and organic acid production) with acid or gaseous sulfur scrubbing.

The introduced bacteria convert the carbon dioxide into organic acids (e.g., acetic acid, butyric acid, propionic acid, lactic acid, and combinations there which may become entrained within the contact liquid 224. As such acids are relatively weak, the pH may decrease to some degree due to the presence of such organic acids, although such decrease may be relatively within about 1-2 pH points relative to what the pH would otherwise be out the action of the organic acid forming bacteria). Furthermore, because the contact liquid 224 may typically include at least some basic components (e.g., a hydroxide and/or carbonate of an alkali or alkali earth metal), such formed organic acids may be neutralized thereby, forming acetate, butyrate, propionate, and/or lactate salts, which may largely precipitate. It may be beneficial to periodically remove such precipitates (e.g., when flushing the scrubbing solution). Such precipitates may be dried, and sold as a value added product (e.g., powdered acetate, butyrate, propionate, and/or lactate salts).

In operation, essentially all of the surfaces in the liquid-gas contact unit 200 may be saturated with the contact liquid 224, such that essentially all surfaces of unit 200 may include the selected bacterial strains disposed thereon. During typical operation of a FGD unit 114 or an acidic scrubber 110, when the absorption or contact liquid 224 is no longer sufficiently effective (e.g., when it is saturated with captured sulfates or other target pollutant), the spent liquid is generally removed for disposal or for capture of a value added side product (e.g., elemental sulfur, sulfuric acid, or the like). In the present embodiments, such spent contact liquid 224 will typically include significant bacteria populations of the desired organic acid forming bacteria. As described above, it may also include precipitated acetates, butyrates, propionates, and/or lactates. In at least some embodiments, viable bacteria within the spent contact liquid may he recovered, for reuse. Any useful precipitates could also be recovered, as desired. Any suitable mechanism may be used for such recovery (e.g., filtration, flocculation, evaporation, or the like).

In addition to inoculation of the liquid-gas contact unit with a bacteria that produces organic acid(s) from the carbon dioxide rich gas stream 214, it is also possible to inoculate the liquid-gas contact unit with additional, differently adapted bacteria, to perform different functions. For example, in an embodiment, the liquid-gas contact unit may also be inoculated with a bacterial strain (or strains) that are adapted to remediate heavy metals, and/or it may be inoculated with one or more bacterial strains that are adapted to inhibit crystal formation (e.g., particularly helpful around holes 252). Additional details describing the use of such bacterial strains in a liquid-gas contact unit are described in U.S. patent application Ser. Nos. 14/839,037 and 15/165,751, each of which has already been incorporated herein by reference in its entirety.

For example, such combination bacterial treatment systems and methods can address issues related to heavy metals capture in liquid-gas contact scrubbers. The additional one or more bacterial strains may be adapted to grow in the liquid-gas contact scrubber and to and to absorb, reclaim, and/or render non-toxic heavy metal wastes from the flue gas that are captured by the scrubber, and/or to inhibit crystal growth (e.g., particularly around holes 252). In some embodiments, all three adaptations of bacteria (for organic acid production, for inhibiting crystal formation, and for heavy metals capture) may be included in the same liquid-gas contact unit, providing all 3 such functions. In other embodiments, such functions may be divided between separate liquid-gas contact units. Any of the described bacterial adaptations may grow and proliferate in the liquid-gas contact unit and form a biofilm on surfaces thereof that is made up of bacteria that perform the identified functions. Alternatively or in addition, the bacteria may exist in a slurry in the contact liquid 224 (e.g., in the reservoir of such liquid, in droplets being sprayed from sprayers 232, 240, and in droplets or liquid layers anywhere else within unit 200. Typically, both biofilm and slurry bacteria may be present.

While described principally in the context of spraying the contact liquid 224 through flue gas 216, it will be appreciated that appropriate liquid-gas contact can be provided by bubbling the flue gas 216 (or other gas stream) through the reservoir of such liquid 224.

Figure 3:
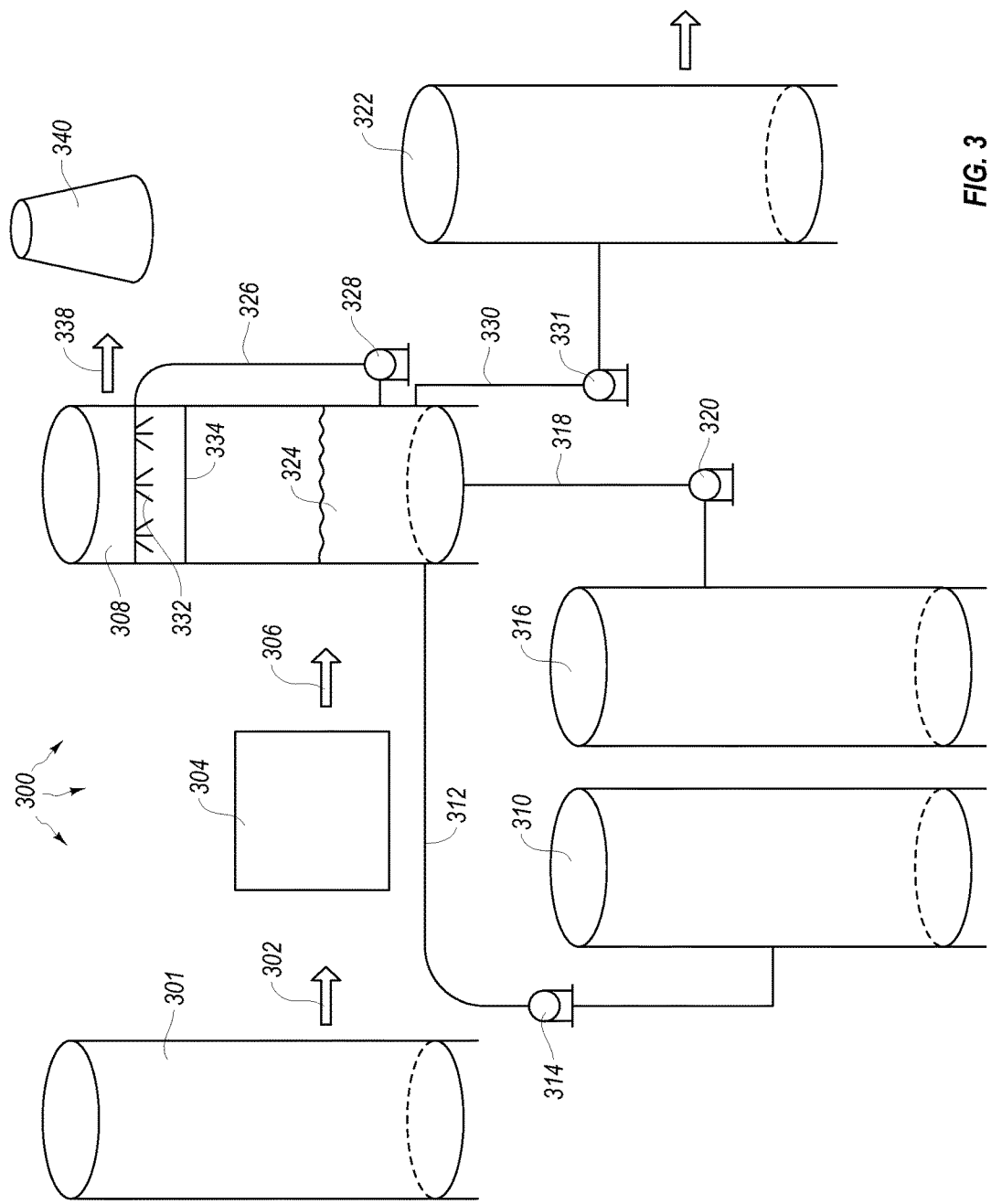
FIG. 3 is a schematic illustration of another liquid-gas contact unit, according to one embodiment of the present disclosure.

Referring now to FIG. 3, a power generation and/or flue gas-handling unit 300 is illustrated that includes another embodiment of a system for inoculating a waste treatment system with bacteria for producing organic acid(s) from gaseous carbon (e.g., $CO_2$, CO) in the gas stream. In the illustrated embodiment, the power generation and/or flue gas-handling unit 300 includes a boiler 301. The boiler 301 may burn coal, oil, natural gas, solid waste, biomass, or another fuel. The boiler 301 produces flue gas 302 that is rich in carbon dioxide. Flue gas 302 may also include significant heavy metals contamination, and/or other pollutants, requiring removal. Particulates (e.g., fly ash) are removed from the flue gas 302 in a particulate precipitator 304 (e.g., an electrostatic precipitator, baghouse, or the like). The flue gas 306 from the precipitator 304 may then be sent to a liquid-gas contact scrubber unit 308. Treated flue gas (338) may be discharged from the liquid-gas contact scrubber unit 308 and sent directly to a discharge stack 340 or to one or more systems for further processing. As will be described in greater detail below, the liquid-gas contact scrubber unit 308 includes at least systems for producing organic acid(s) from the gaseous carbon in the gas stream. It may further include systems for absorbing, reclaiming, and/or rendering non-toxic heavy metal wastes, and/or inhibiting crystal formation within unit 308.

Similar to the systems discussed in reference to FIGS. 2A and 2B, the liquid-gas contact scrubber unit 308 includes a vessel, a reservoir of absorption liquid 324, a recirculating system (i.e., pump 328 and recirculating line 326), sprayers 332, and contact surface 334. In addition, the system 300 is shown as including an external reservoir 310 of absorption liquid 324 that can be used via line 312 and pump 314 to replenish spent absorption liquid 324 in the scrubber 308. Likewise, the system 300 is shown as including an external reservoir 322 that can be used for withdrawing spent absorption liquid 324 from the scrubber 308 via line 330 and pump 331. While the system 300 shows a tank 322, it will be understood that the external reservoir for spent desulfurization or other reactive agent could include or be a holding facility such as a pond or waste lagoon.

The system 300 also includes means for inoculating the scrubber 308 with an inoculum that includes one or more bacterial strains that are adapted to grow in the scrubber 308 and produce organic acid(s) therein. In the illustrated embodiment, the means for inoculating the scrubber 308 includes an external holding vessel 316 that is designed to hold the bacteria until they are added to the scrubber unit 308. In addition, the means for inoculating includes a feed system that may include devices for delivering a dry or liquid bacterial preparation to the scrubber 308. In the illustrated embodiment, the feed system includes a feed line 318 that feeds into the reservoir 324 of the scrubber 308 and a pump or other feeder 320.

In the case of a dry bacterial preparation, the feeder 320 may be screw auger, conveyor, or the like that is configured for conveying a dry powder. Likewise, the feeder 320 may be configured to withdraw a dry bacterial preparation from the vessel 316, mix it with aqueous media (e.g., water), and deliver a rehydrated bacterial preparation to the scrubber 308. Alternatively, if the vessel 316 includes liquid bacterial preparation, the feeder 320 may be a pump designed to deliver liquid to the scrubber 308. While described in the context of delivering the bacterial strain(s) adapted to produce organic acids, it will be appreciated that similar configurations may be used to deliver bacterial strain(s) adapted to remediate heavy metals and/or to inhibit crystal formation. In some embodiments, two or more differently adapted bacterial strains may be stored and/or conveyed through the same or a single system.

The feed system (i.e., line 318 and the feeder 320) may be designed to deliver an initial inoculum to the scrubber 308 followed by periodic re-inoculations designed to maintain a population of bacteria in the scrubber 308. Following the initial inoculation, the scrubber 308 may be re-inoculated on a selected schedule. Thus, the feed system may be designed to feed bacteria from the vessel 316 to the scrubber 308 at a selected constant rate (i.e., continuous addition of fresh bacteria) or on an hourly, daily, or weekly re-inoculation schedule (i.e., periodic addition of fresh bacteria). Such addition of fresh bacterial may be automated.

In an embodiment, the feed system (i.e., line 318 and the feeder 320) may be designed to deliver a selected amount of bacteria to the scrubber 308. In one embodiment, the inoculum has a selected volume and a selected bacterial cell density in a range of 0.01 weight % (wt %) to 10 wt %, 0.05 wt % to 5 wt %, 0.1 wt % to 3 wt %, 0.2 wt % to 2 wt %, 0,25 wt % to 1 wt %, or 0.3 wt % to 0.5 wt %, for any of the bacterial adaptations, individually, or collectively. In an embodiment, each of the included bacterial adaptations may individually fall within the above ranges, such that an overall bacterial loading may be double or triple the above ranges. The volume of the inoculum will vary depending on factors such as, but not limited to, the size of the liquid-gas contact unit (e.g., scrubber), the chemistry utilized in the liquid-gas contact unit (e.g., scrubber), the temperature of the gas stream, etc.

In a typical liquid-gas contact unit, the initial inoculum may have a volume of about 50-200 gallons (e.g., 100 gallons) of bacterial solution at about 0.2 wt % to 2 wt % (e.g., 0.3 wt %) followed by weekly maintenance doses of about 10-100 gallons (e.g., 50 gallons) of bacterial solution at about 0.2 wt % to 2 wt % (e.g., 0.3 wt %), for each of the included specific bacterial adaptations. In other words, the initial inoculum of the organic acid producing bacteria may have a volume of about 50-200 gallons (e.g., 100 gallons) of bacterial solution at about 0.2 wt % to 2 wt % (e.g., 0.3 wt %) followed by weekly maintenance doses of about 10-100 gallons (e.g., 50 gallons) of bacterial solution at about 0.2 wt % to 2 wt % (e.g., 0.3 wt %). Where included, the initial inoculum of a bacteria for inhibiting crystal formation may have a volume of about 50-200 gallons (e.g., 100 gallons) of bacterial solution at about 0.2 wt % to 2 wt % (e.g., 0.3 wt %) followed by weekly maintenance doses of about 10-100 gallons (e.g., 50 gallons) of bacterial solution at about 0.2 wt % to 2 wt % (e.g., 0.3 wt %). Where included, the initial inoculum of the bacteria adapted to remediate heavy metals may have a volume of about 50-200 gallons (e.g., 100 gallons) of bacterial solution at about 0.2 wt % to 2 wt % (e.g., 0.3 wt %) followed by weekly maintenance doses of about 10-100 gallons (e.g., 50 gallons) of bacterial solution at about 0.2 wt % to 2 wt % (e.g., 0.3 wt %).

Methods for production of organic acid(s) from a gas stream rich in carbon dioxide (e.g., from a power plant) have been described in reference to FIGS. 1-3. Such methods include providing a gas stream rich in carbon dioxide, introducing the gas stream into a liquid-gas contact unit, preparing an inoculum comprising a bacterial strain adapted to reduce carbon dioxide in the gas stream and to produce organic acid(s) therefrom, and inoculating the liquid-gas contact unit with a first amount of the inoculum such that the bacteria are present therein to consume carbon dioxide from the gas stream and to produce one or more organic acids therefrom. Such methods may further include preparing bacterial strains that are differently adapted (e.g., to remediate heavy metals, and/or to inhibit crystal formation in the liquid-gas contact unit), and inoculating the liquid-gas contact unit with those inoculations, as well. It will be appreciated that the embodiments described in reference to FIGS. 1-3 are merely illustrative and that there are a number of other liquid-gas contact units (or even other waste treatment units) that can be used at industrial facilities (e.g., at power plants) with which the methods described herein can be utilized.

In one embodiment, the inoculum has a selected volume and a selected bacterial cell density in a range of 0.01 weight % (wt %) to 10 wt %, 0.05 wt % to 5 wt %, 0.1 wt % to 3 wt %, 0.2 wt % to 2 wt %, 0.25 wt % to 1 wt %, or 0.3 wt % to 0.5 wt %. The volume of the inoculum will vary depending on factors such as, but not limited to, the size of the liquid-gas contact unit or other waste treatment unit, the chemical environment in the liquid-gas contact unit or other waste treatment unit, the temperature of the gas stream, etc. As described above, any of the particularly adapted initial inoculums may have a volume of about 50-200 gallons (e.g., 100 gallons) of bacterial solution at about 0.2 wt % to 2 wt % (e.g., 0.3 wt %) followed by weekly maintenance doses of about 10-100 gallons (e.g., 50 gallons) of bacterial solution at about 0.2 wt % to 2 wt % (e.g., 0.3 wt %). For heavy metals remediation, the waste treatment unit that is inoculated may be a waste lagoon in addition to, or instead of the liquid-gas contact unit. The inoculum size appropriate for a waste lagoon may be in the range of hundreds of gallons to thousands of gallons, depending on the size of the lagoon and the wastes present in the lagoon.

As described above, the methods may include reinoculating the liquid-gas contact unit or other waste treatment unit with at least a second amount of the inoculum. In one embodiment, the reinoculating occurs in a range of daily to weekly. In one embodiment, the inoculum may he provided in a dry form. In such an embodiment, the method may further include mixing the inoculum with an aqueous medium prior to inoculating the at least one waste treatment unit with the inoculum. In another embodiment, the inoculum may be provided in a liquid form wherein the bacterial strain is suspended in an aqueous medium.

In one embodiment, the methods described herein may include removing the bacteria from the liquid-gas contact unit or other waste treatment unit and, for example, drying the waste material and the bacteria and disposing of (e.g., burying) the dried waste material in a dry waste disposal unit. Removed bacteria could also be disposed of, or could be reclaimed, for reuse of viable bacteria.

The methods described herein may further include allowing the bacteria to proliferate in the liquid-gas contact unit or other waste treatment unit for a selected period of time, recovering the bacteria from the liquid-gas contact unit or other waste treatment unit. Bacteria used to remediate heavy metals may have the heavy metals recovered therefrom. Bacteria used to inhibit crystal formation and/or produce organic acids may be disposed of, or if such bacteria are viable, they may be separated from other materials of the waste stream, and reused.

The methods described herein may include reinoculating the liquid-gas contact unit or other waste treatment unit with a fresh bacterial inoculum. Likewise, any one of the liquid-gas contact unit or other waste treatment units described herein may be taken offline for, for example, cleaning, repair, or replacing contact liquid or other waste treatment agent. In such cases, the method may include recharging with contact liquid and the gas stream, and reinoculating.

In one embodiment, the bacteria are selected for their ability to grow and proliferate in the liquid-gas contact unit or other waste treatment unit and to convert at least a portion of carbon dioxide in the gas stream to organic acid(s). In one embodiment, the bacteria in the at least one waste treatment reduce carbon dioxide concentration by at least 5%, at least 10%, at least 15%, at least 20%, at least 25%, at least 30%, at least 35%, at least 40%, at least 45%, at least 50%, more than 50%, or at least 55%, Even higher reductions may be achievable by staging two or more liquid-gas contact units in series. For example, reductions of at least 60%, at least 65%, at least 70%, at least 75%, at least 80%, at least 85%, at least 95%, or at least 95% may be possible thereby. For example, the test results described below show more than a 55% reduction in carbon dioxide with just a single pass through a liquid-gas contact unit.

Examples of bacterial strains adapted to produce one or more organic acids (e.g., one or more of acetic acid, butyric acid, propionic acid, lactic acid) include, but are not limited to *Pediococcus, Propionibacterium*, and combinations thereof. In a preferred embodiment, the bacterial strain adapted to produce one or more organic acids may include *Pediococcus acidilacti, Propionibacterium freudenreichii*, variants thereof, or combinations thereof.

Examples of bacterial strains adapted to inhibit crystal formation include *Rhodococcus, Bacillus, Pseudomonas, Clostridia, Burkholderia, Oceanospirillum, Neptunomonas, Alcanivorax, Acetobacter* sp., *Acidiothiobacillus* sp., *Acetobacterium* sp., *Clostridia* sp., *Pseudomonas* sp., *Bacillus* sp., *Halobacteria, Halococcus, Chromohalobacter, Methanosarcina* sp., *Methanococcus* sp., *Acetobacterium*, sp., *Clostridia* sp., *Pseudomonas* sp., *Micrococcus, Achromobacter, Flavobacterium, Bactericides, Serratia, Alcaligenes, Cellulomonas*, and variants thereof. Preferably, the bacterial strains adapted to inhibit crystal formation include *Bacillus subtilis, Bacillus chitinosporus*, variants thereof, or combinations thereof.

Examples of bacterial strains adapted to remediate heavy metals include *Rhodococcus, Bacillus, Pseudomonas, Clostridia, Burkholderia, Oceanospirillum, Neptunomonas, Alcanivorax, Acetobacter* sp., *Acidiothiobacillus* sp., *Acetobacterium* sp., *Clostridia* sp., *Pseudomonas* sp., *Bacillus* sp., *Halobacteria, Halococcus, Chromohalobacter, Methanosarcina* sp., *Methanococcus* sp., *Acetobacterium*, sp., *Clostridia* sp., *Pseudomonas* sp., *Micrococcus, Achromobacter, Flavobacterium, Bacterioides, Serratia, Alcaligenes, Cellulomonas*, and variants thereof. In a preferred embodiment, bacterial strains adapted to remediate heavy metals include one or more of *Bacillus amyloliquefaciens, Bacillus licheniformis*, variants thereof, or combinations thereof.

In one embodiment, the methods described herein may include removing the organic acids produced (or salts thereof) from the liquid-gas contact unit or other waste treatment unit, for example, by filtering or otherwise separating precipitated organic acid salts from the scrubber solution, and then drying the precipitated product. Such materials could be disposed of (e.g., buried), although it may be preferred to sell such precipitates as a value added product.

IV. Examples

Example 1 demonstrates use of the bacteria described herein to produce organic acid(s) from the carbon dioxide in a gas stream rich in carbon dioxide. Examples 2-3 demonstrate remediation of heavy metals in such a gas stream, and Example 4 demonstrates inhibition of crystal formation in a liquid-gas contact unit.

Example 1

Bacterial strains were assayed for their ability to produce organic acid(s) from a gas stream rich in carbon dioxide in a liquid-gas contact unit. A control and a treatment sample were compared to determine whether production of organic acids and reduction in carbon dioxide concentration could be demonstrated after microbial addition to the liquid solution (in distilled water). The control included no added microbial solution. The microbial solution included *Pediococcus acidilacti* and *Propionibacterium freudenreichii*. Target bacteria concentration of the *Pediococcus acidilacti* and *Propionibacterium freudenreichii* was $5.0 \times 10^5$ to $1.5 \times 10^7$ CFU/mL (e.g., 500,000-1,500,000 CFU/mL). Test protocol for both the control and treatment sample was as follows:

Fill graduated cylinder with glass marbles to approximately 50% of internal area.

Attach a metered $CO_2$ pump to the bottom inlet port to slowly bubble in 2.5%-5% $CO_2$.

Attach a $CO_2/O_2$ meter to top exit port to measure $CO_2$ concentration changes.

Add liquid carrier solution (power plant water) to the graduated cylinder to cover the glass marbles completely.

A microbial cocktail including the two microorganisms (*Pediococcus acidilacti* and *Propionibacterium freudenreichii*) was transferred to the liquid carrier solution of the test solution at approximately $1 \times 10^6$ CFU/mL concentration. No microbes were added to the control.

A pH measurement was made every 4 hours to determine pH changes in the solution.

The duration of the trial was approximately 7 days to allow for microbial colonization on the marble surface area. The greater the surface area contact, the greater the potential for $CO_2$/microbial interaction and accelerated residence time contact.

After 3 days (3 days post inoculation), $CO_2$ measurements were recorded at the top exit of the port every 5-6 hours.

Continue measuring $CO_2$ concentrations.

Measurements were taken periodically of $CO_2$ and $O_2$ concentration, as well as pH. Twelve readings were taken over the 4 week test period. The average of the measured readings were as shown below in Table 1.

TABLE 1

| | $CO_2$ (In) concentration | $CO_2$ (Out) concentration | $CO_2$ % change | Solution pH |
|---|---|---|---|---|
| Control | 1100 ppm | 1068 ppm | −2.90% | 7.2 |
| Microbial Treatment | 1120 ppm | 485 ppm | −56.6% | 6.5 |

Dissolved oxygen concentration in solution may be expelled out the surface of the solution, or may be used by the bacteria to complete its aerobic respiration cascade. It is believed that the carbon-oxygen bonds in $CO_2$ (or CO) bubbled through the water solution are broken by the microbes. Both carbon and oxygen are used by the microbes to complete their respiration cycling and in the generation of the formed organic acids. Oxygen in the water may be important as a final electron acceptor, helping to maintain a healthy solution environment and to facilitate microbial division. The carbon of the $CO_2$ bubbled through during the test was used by the microorganisms to assemble new proteins, cellular membranes, and to build organic acid molecules. The production of organic acids slightly dropped the pH in the test solution, as shown above, indicating that the new acids are being formed by taking the carbon from $CO_2$ and linking such carbon atoms together to make newly formed weak organic acids. Acetic acid, as well as butyric acid, propionic acid, and lactic acid were formed.

These data demonstrate that the bacteria described herein are able to produce organic acid(s) from the carbon dioxide in a gas stream rich in carbon dioxide. The 57% reduction in $CO_2$ concentration in the gas stream exiting the test solution as compared to when it entered the test solution is particularly notable. Even higher $CO_2$ reductions could be achieved by placing another test solution in series with the first test solution.

Example 2

Bacterial strains were assayed for their ability to remediate heavy metals in a power plant sludge slurry from a waste lagoon or gas-liquid contact scrubber (e.g., sulfate sludge from a FGD unit). A control and a treatment sample were compared to determine whether a reduction of heavy metals could be demonstrated after microbial addition to the slurry. A microbial treated sample=95 grams sludge slurry+5 grams microbial solution and an untreated control sample=100 grams of sludge slurry only. The microbial solution included *Bacillus amyloliquefaciens* and *Bacillus licheniformis*. The assay methodology was as follows:

Ninety-five grams of the wet sludge material was transferred into a 500 ml beaker;

Five grams of a selected microbial solution was transferred into the beaker and mixed thoroughly with the sludge material to form a homogenous suspension;

The homogenous sample placed into an incubator set to 40° C.;

The mixture was allowed to incubate for at least 12 days with slight stirring every 2 days; and Both the treated and control samples were submitted for heavy metal analysis (e.g., atomic adsorption spectroscopy or atomic emission spectroscopy).

Example 3

Sludge residue originating from power plant waste by-products were treated with specialized heavy metal and sludge remediating bacteria using the same microbes as in Example 2. After allowing for microbial bioremediation, both untreated and treated samples were submitted to independent third party laboratories for a full heavy metals analysis. Inductively Coupled Plasma-Atomic Emissions Spectrometry (ICP-AE) tests were performed to determine the presence and amount of heavy metal in the contaminated sludge before and after treatment with the bacteria. Results are shown below

TABLE 2

Heavy Metal Assay
(Liquid Form; 2015; Untreated Control vs. Microbial Treated)

| Heavy Metals (Total) | Untreated (mg/kg ppm) | Microbial Treated (mg/kg; ppm)* | % Change |
|---|---|---|---|
| Mercury | n.d. | n.d. | — |
| Zinc | 43.5 | 26.1 | −40% |
| Selenium | 3.08 | 1.14 | −63% |
| Lead | 8.6 | 3.1 | −64% |
| Nickel | 10.2 | 4.2 | −59% |
| Molybdenum | 1.1 | n.d. | −100% |
| Cobalt | 3.31 | 1.54 | −53% |
| Cadmium | 0.65 | n.d. | −100% |
| Arsenic | 4.02 | n.d. | −100% |

Analytical Methods: EPA 6010B/7471A (Midwest Laboratories, Inc.)
*Microbial Treatment: Sodium sulfide sludge and carry over residue in a liquid form.
Trial duration: 28 days

TABLE 3

Heavy Metal Assay
(SOLID Form; 2015; Untreated Control vs. Microbial Treated)

| Heavy Metals (Total) | Untreated (mg/kg; ppm) | Microbial Treated* (mg/kg; ppm) | % Change |
|---|---|---|---|
| Mercury | 0.02 | n.d. | −100% |
| Barium | 34.8 | 8.12 | −76% |
| Selenium | 6.16 | 1.16 | −81% |
| Lead | n.d. | n.d. | n.d. |
| Silver | n.d. | n.d. | n.d. |
| Chromium | 1.42 | 0.728 | −48% |
| Cadmium | n.d. | n.d. | n.d. |
| Arsenic | 5.67 | 2.50 | −56% |

Analytical Methods: EPA 6010B/7471A (Chemtech-Ford Laboratories)
*Microbial Treatment: Sodium sulfide sludge and carry over residue in a dry form.
Trial Duration: 21 days

TABLE 4

Heavy Metal Assay
(Liquid Form; Scrubber liquid; 2015;
Untreated Control vs. Microbial Treated)

| Heavy Metals (Total) | Untreated (mg/kg; ppm) | Microbial Treated* (mg/kg; ppm) | % Change |
|---|---|---|---|
| Mercury | 0.02 | 0.003 | −85% |
| Barium | 34.8 | 6.27 | −82% |
| Selenium | 6.16 | 5.98 | −3% |
| Lead | n.d. | n.d. | n.d. |
| Silver | n.d. | n.d. | n.d. |
| Chromium | 1.42 | 0.135 | −90% |
| Cadmium | n.d. | n.d. | n.d. |
| Arsenic | 5.67 | 2.66 | −53% |

Analytical Methods: EPA 6010B/7471A (Chemtech-Ford Laboratories)
*Microbial Treatment: Sodium sulfide sludge and carry over residue in a dry form.
Trial Duration: 14 days

TABLE 5

Heavy Metal Assay - 12 day reduction

| Analysis | Untreated mg/kg | Treated 12 day mg/kg | % Reduction | Method |
|---|---|---|---|---|
| Mercury | Not Detected | Not Detected | n/a | EPA 7471 |
| Zinc | 43.5 | 26.1 | 40% | EPA 6010 |
| Selenium | 3.08 | 1.14 | 63% | EPA 6010 |
| Lead | 8.60 | 3.10 | 64% | EPA 6010 |
| Nickel | 10.2 | 4.20 | 59% | EPA 6010 |
| Molybdenum | 1.10 | Not Detected | 100% | EPA 6010 |
| Cobalt | 3.31 | 1.54 | 53% | EPA 6010 |
| Cadmium | 0.65 | Not Detected | 180% | EPA 6010 |
| Arsenic | 4.02 | Not Detected | 100% | EPA 6010 |

These data demonstrate that the bacteria described herein are able to remediate heavy metals in the systems and methods described herein.

Example 4

Bacterial strains selected from amongst those described in the present application were tested in order to understand the scope of the problems associated with crystalline buildup in an FGD unit and to assess the ability of such bacterial strains to inhibit or prevent crystalline buildup. The inventor tested selected bacterial strains using the methods and systems described herein to assess their ability to inhibit buildup of crystalline materials of an FGD unit of a typical working power plant.

The FGD unit on a generation unit at a particular power plant experiences large amounts of buildup that restricts the flow of the flue gas. This buildup is primarily on the perforated trays and the inlet duct. The various types of buildup result in increased differential pressure in the scrubber vessel. These increased pressure differentials cause multiple problems. Some of the potential problems caused by the differential pressures are: flipped trays, increased particulate emissions attributed to the scrubber, unit outages to clean trays and increased operation and maintenance cost associated with having to take the generation unit offline so that the FGD unit can be cleaned.

Crystalline buildup in the unit was seen to be particularly problematic on the fluid/gas contactor trays. The buildup on the perforated trays (see, e.g., FIG. 2B) is on the underside of the holes in the trays. The buildup starts from the outside of the perforations and grows towards their center, decreasing the diameter of the perforations. This increases the differential pressure across the trays. This pressure, although small (e.g., on the order of a couple of water inches), is enough to lift and flip the trays. There is a need to prevent the tray flipping. In order to do this, the holes in the perforated trays must remain clean. It is the restriction of the perforated trays that increases the differential pressures. The flipped trays are a problem when the time comes to clean the scrubber, and they also result in increased particulate emissions due to higher gas velocities.

When the time to clean the scrubber comes, the plant safety team has typically had to rig ropes for entry into the FGD unit to right the flipped trays. This has cost an average of three hours of work and outage time. That time spent delays the entirety of the clean. All time spent in delaying the scrubber clean results in one of two things: an extended outage, or a less thorough clean. The extended outage costs the company lost generation. A calculation for the lost generation for routine maintenance has been given in Equation 1. Routine maintenance does not include a complete clean of the unit. A clean that is not complete results in more frequent outages to clean the scrubber.

Lost Generation ($)=Price per megawatt (MW)×time delayed×MW possible $=$25/hr×3 hr×280 MW $=$21,000    Equation 1

The increased particulate emissions, as a result of the flipped trays, are a compliance issue. An integral part of the plant's environmental permitting is Mercury and Air Toxics Standards (MATS). If the particulate emissions increase enough, the plant is no longer complaint with MATS. Non-compliance can result in more unit outages. In most years there are 2-3 maintenance outages per year in which the unit has been brought offline specifically to clean and maintain the FGD unit. These outages result in a loss of 280 MW for 36-48 hours. According to Equation 1, this represents a cost of ~$250,000 to ~$335,000. In addition to the cost of lost generation, there is an average cost of about $30,000 for contractors to perform a clear of the FGD unit. Conservatively, it is believed that at least one of these yearly outages could be avoided by using the bacterial methods and systems described in the present application. Avoiding just one of these outages would represent a cost savings of ~$250,000 to ~$335,000 in generation time alone.

Microbe Theory:

In order to test whether the bacterial strains described in the present application could address some of the problems with crystalline buildup in the FGD unit, plant lab personnel were given a sample of *Bacillus subtilis* and *Bacillus chitinosporus* and variants thereof for testing. The theory behind the microbe is to form a bio-film, or protective layer, on all of the metal parts in the FGD and to then prevent or inhibit buildup of crystalline deposits on the various surfaces in the FGD unit. It is believed that the bio-film forming bacteria may be able to consume the buildup-causing compounds in the recycle slurry. If build up continues forming on the underside of the trays, the crystals would be more soluble and more easily removed by the under tray spray system. This should prevent the crystalline buildup on the underside of the trays. In consequence, the holes in the perforated trays should remain clear and differential pressure should stay low.

Test Results:

There were two sets of tests that have been completed on the microbes so far with two more in the process of being tested. The initial test yielded results showing that the crystalline structure of the buildup is favorably changed in the presence of the microbes. It also illustrated that the steel was protected in such a way that the would-be-buildup was easily rinsed way. A control sample was tested in the absence of microbes to illustrate what the current conditions of the FGD unit would look like under the exact same conditions.

It was observed that the control test yielded long, thin crystals that intertwined to form a crystalline buildup that is very dense and is very difficult to break down. The test sample in the presence of the microbes yielded very small crystals that appeared to be irregular cubic shapes. These smaller crystals were easily rinsed way as they had no definite crystal structure.

The second test was performed to confirm the results of the previous test. Having already established what happened in the absence of microbes, we did not feel a need to run a second control sample. We ran a second test sample with the prescribed concentration of microbes. The other sample was performed with an excess of microbes to simulate what may happen if the microbes were to overpopulate the scrubber or to be grossly overfed inadvertently.

The sample with an excess of microbes indicated that there would be no operational issues with an over feed situation. It is assumed that the overpopulation of the microbes caused them to have a shortage of consumables in their ecosystem of the test. This added credibility to the value of our test dose concentration. The other test, with the prescribed amount of microbes, was performed in the same manner as the first test.

The results were nearly identical to the first test. The crystals were small and easily rinsed away during the cleanup step. There was one slight difference as compared to the first test and that is that the samples of recycle slurry used in the second test had much more ash. This ash resulted in the crystals forming a cake of crystal and ash. This cake was easily broken with the gentle flow of water and dispersed into ash and crystals. The ash was easily rinsed away and then the crystals fell apart. This confirmed the results of the first tests performed. Videos were taken of the rinsing process for second test.

It is worthwhile to comment on the microscopic structure of the two types of crystals. When viewed under a 10× power microscope, the difference in the size and shape of the crystals is very evident. Please note that the larger crystals (absence of microbes) are closely bonded to one another. The smaller crystals (presence of microbes) are loose and independent of one another. They were held together with the ash as the test sample dried out at the conclusion of the test cycle. This results in the easy rinsing that has been mentioned.

Practical Application:

The tested microbes and the related microbes described in the present application and the crystalline structure that results from their presence has many potential benefits for the particular plant's FGD unit and for RID units in general. The following outlines the benefits:

Less buildup on the underside of the trays.
Decreased differential pressure (DP) across the trays.
Fewer flipped trays,
Decreased time in outages to flip trays back over.
Lower gas velocities in the vessel.
Fewer PM emission attributed to the scrubber.
More efficient $SO_2$ reduction.
Safer working condition during outages.
Cleaner demisters.
Fewer unit maintenance outages due to high DP.
Less time spent cleaning trays.
Longer tray life.
Shorter outages.
Less buildup in the scrubber inlet and ducts.
Decreased inlet pressure.
Fewer maintenance outages due to high inlet pressure.
Lower gas velocities.
Decreased PM attributed to scrubber.
Less time cleaning inlets.
Shorter outages.

The increased unit availability due to decreased outage time is one of the biggest benefits to the application of these microbes. As noted above, preventing just one 36-48 hour outage per year represents a cost savings of up to ~$250,000 to ~$335,000 in generation time alone. Likewise, the chemical environment in a FGD unit is quite harsh. The formation of a protective biofilm on the metal parts in the FGD unit results in a potential for great payoff in the remaining life of the scrubber.

There is also a great benefit to be found in the decrease in cleaning time. The companies that clean scrubber units charge by the hour. If the material is easier to remove, the clean will cost significantly less. It is difficult to quantify the money saved in the time to clean the scrubber due to the fact that a clean in the presence of the microbes has never been performed. If laboratory tests are representative of what can be expected in the scrubber, it is not unfair to assume that the outage time to clean would be reduced by one half. It is possible that with the systems and methods described herein that outages due to crystalline buildup could be prevented entirely.

There is a potential that the addition of the microbes could make the FGD unit self-cleaning. The nature of the liquid flow in the scrubber is very turbulent, in our tests the ash caused the crystals to form a cake on the bottom of the vessel. In the turbulent environment of the scrubber, it is expected that the ash would never have the opportunity to settle. Thus the cake structure should never form, leaving only crystals that can easily be broken apart. If this is the case, the need for scrubber cleans could be completely mitigated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for producing one or more short chain weak organic acids, the method comprising:
   providing a gas stream rich in carbon dioxide;
   introducing the gas stream into a liquid-gas contact unit;
   preparing an inoculum that comprises a first bacterial strain adapted to reduce a concentration of carbon dioxide in the gas stream, and to produce one or more organic acids therefrom, and
   inoculating the liquid-gas contact unit with a first amount of the inoculum such that the bacteria are present therein to consume carbon dioxide from the gas stream and to produce one or more organic acids therefrom, the one or more organic acids comprising one or more of acetic acid, butyric acid, propionic acid, or lactic acid.

2. The method of claim 1, wherein bacteria does not produce any appreciable volume of biogas.

3. The method of claim 1, wherein the bacteria is adapted to reduce a concentration of carbon dioxide in the gas stream by at least 10%.

4. The method of claim 1, wherein the bacteria is adapted to reduce a concentration of carbon dioxide in the gas stream by at least 30%.

5. The method of claim 1, wherein the bacteria is adapted to reduce a concentration of carbon dioxide in the gas stream by at least 50%.

6. The method of claim 1, wherein the first bacterial strain is at least one a bacterial, proteobacterial, or archaeal species comprising *Pediococcus, Propionibacterium,* variants thereof, or combinations thereof.

7. The method of claim 1, wherein the first bacterial strain comprises *Pediococcus acidilacti, Propionibacterium freudenreichii,* variants thereof, or combinations thereof.

8. The method of claim 1, the method further comprising inoculating the liquid-gas contact unit with a second inoculum of a second bacterial strain adapted to inhibit crystalline formation in the liquid-gas contact unit;
   wherein the gas stream is a flue gas stream, the liquid-gas contact unit is a liquid-gas contact flue gas desulfurization "FGD" unit comprising:
      a vessel with a flue gas inlet and a flue gas outlet and a liquid reservoir containing a liquid flue gas treating agent;
      a recirculation/spray system configured to circulate the liquid flue gas treating agent through the vessel;
      one or more contact surfaces in the vessel configured for contacting the flue gas and the liquid flue gas treating agent recirculated from the reservoir;
   wherein the first bacterial strain and the second bacterial strain are disposed in the liquid reservoir containing the liquid flue gas treating agent, wherein both bacterial strains are adapted to grow in the liquid flue gas treating agent, wherein the second bacterial strain forms a biofilm on one or more contact surfaces in the FGD unit in order to inhibit crystalline buildup therein; and
   wherein the first bacterial strain is at least one bacterial, proteobacterial, or archaeal species comprising *Pediococcus acidilacti, Propionibacterium freudenreichii,* variants thereof, or combinations thereof, and wherein the second bacterial strain is at least one bacterial, proteobacterial, or archaeal species comprising *Bacilus subtilis, Bacillus chitinosporus,* variants thereof, or combinations thereof.

9. The method of claim 8, further comprising inoculating the liquid-gas contact unit with a third bacterial strain, wherein the third bacterial strain is adapted to remediate heavy metals, and wherein the third bacterial strain is at least one bacterial, proteobacterial, or archaeal species comprising *Bacilus amyloliquefaciens, Bacillus licheniformus,* variants thereof, or combinations thereof.

10. A method comprising:
    providing a gas stream rich in carbon dioxide;
    introducing the gas stream into a liquid-gas contact unit;
    preparing an inoculum that comprises a first bacterial strain adapted to reduce a concentration of carbon dioxide in the gas stream, and to produce one or more organic acids therefrom, and
    inoculating the liquid-gas contact unit with a first amount of the inoculum such that the bacteria are present therein to consume carbon dioxide from the gas stream and to produce one or more organic acids therefrom;
    inoculating the liquid-gas contact unit with a second inoculum of a second bacterial strain adapted to inhibit crystalline formation in the liquid-gas contact unit;
    wherein the gas stream is a flue gas stream, the liquid-gas contact unit is a liquid-gas contact flue gas desulfurization "FGD" unit comprising:
       a vessel with a flue gas inlet and a flue gas outlet and a liquid reservoir containing a liquid flue gas treating agent;
       a recirculation/spray system configured to circulate the liquid flue gas treating agent through the vessel;
       one or more contact surfaces in the vessel configured for contacting the flue gas and the liquid flue gas treating agent recirculated from the reservoir; and
    wherein the first bacterial strain and the second bacterial strain are disposed in the liquid reservoir containing the liquid flue gas treating agent, wherein both bacterial strains are adapted to grow in the liquid flue gas treating agent, wherein the second bacterial strain forms a biofilm on one or more contact surfaces in the FGD unit in order to inhibit crystalline buildup therein.

11. The method of claim 10, wherein the first bacterial strain is at least one bacterial, proteobacterial, or archaeal species comprising *Pediococcus acidilacti, Propionibacterium freudenreichii*, variants thereof, or combinations thereof.

12. The method of claim 11, wherein the second bacterial strain is at least one bacterial, proteobacterial, or archaeal species comprising *Bacilus subtilis, Bacillus chitinosporus*, variants thereof, or combinations thereof.

13. The method of claim 12, further comprising inoculating the liquid-gas contact unit with a third bacterial strain, wherein the third bacterial strain is adapted to remediate heavy metals.

14. The method of claim 13, wherein the third bacterial strain is at least one bacterial, proteobacterial, or archaeal species comprising *Bacilus amyloliquefaciens, Bacillus licheniformus*, variants thereof, or combinations thereof.

* * * * *